United States Patent
Park et al.

(10) Patent No.: US 9,644,185 B2
(45) Date of Patent: May 9, 2017

(54) CELL PERMEABLE FUSION PROTEIN FOR FACILITATING REPROGRAMMING INDUCTION AND USE THEREOF

(71) Applicants: SNU R&DB Foundation, Seoul (KR); NANO INTELLIGENT BIOMEDICAL ENGINEERING CORPORATION CO. LTD., Chungcheongbuk-do (KR)

(72) Inventors: Yoon Jeong Park, Seoul (KR); Gene Lee, Seoul (KR); Hyun Nam, Seoul (KR); Jin Sook Suh, Seoul (KR); Chong-Pyoung Chung, Seoul (KR); Jue-Yeon Lee, Gyeonggi-do (KR)

(73) Assignees: SNU R&DB FOUNDATION, Seoul (KR); NANO INTELLIGENT BIOMEDICAL ENGINEERING CORPORATION CO. LTD., Chungcheongbuk-Do (KR)

(*) Notice: Subject to any disclaimer, the term of this patent is extended or adjusted under 35 U.S.C. 154(b) by 0 days.

(21) Appl. No.: 14/470,013

(22) Filed: Aug. 27, 2014

(65) Prior Publication Data
US 2015/0064783 A1    Mar. 5, 2015

(30) Foreign Application Priority Data
Aug. 28, 2013  (KR) .......................... 10-2013-0102195

(51) Int. Cl.
- *C12N 5/00* (2006.01)
- *C12N 5/074* (2010.01)
- *C07K 14/47* (2006.01)
- *C07K 7/08* (2006.01)

(52) U.S. Cl.
CPC ............. *C12N 5/0696* (2013.01); *C07K 7/08* (2013.01); *C07K 14/4702* (2013.01); *C07K 2319/00* (2013.01); *C07K 2319/10* (2013.01); *C07K 2319/80* (2013.01); *C07K 2319/85* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2502/1364* (2013.01); *C12N 2506/1361* (2013.01)

(58) Field of Classification Search
None
See application file for complete search history.

(56) References Cited

U.S. PATENT DOCUMENTS

| | | | |
|---|---|---|---|
| 8,796,219 B2 * | 8/2014 | Park ................. | A61K 47/48315 514/19.3 |
| 2007/0071677 A1 * | 3/2007 | Park ..................... | A61K 38/168 424/1.69 |
| 2010/0298536 A1 * | 11/2010 | Park ..................... | A61K 49/0041 530/326 |
| 2012/0095188 A1 * | 4/2012 | Jo ........................ | C07K 14/4702 530/350 |
| 2014/0377243 A1 * | 12/2014 | Chung ................. | C12N 9/0089 424/94.3 |

FOREIGN PATENT DOCUMENTS

| | | | |
|---|---|---|---|
| EP | 2615105 A1 | 7/2013 |
| KR | 10-2005-0011288 A | 1/2005 |
| KR | 1020090123768 A | 12/2009 |
| WO | 2005007860 A1 | 1/2005 |
| WO | 2009045062 A1 | 4/2009 |
| WO | 2010059806 A3 | 5/2010 |
| WO | 2010115052 A2 | 10/2010 |
| WO | 2010138517 A1 | 12/2010 |

OTHER PUBLICATIONS

Xu et al. Nat. Biotechnol. 2001;19, 971-974.*
Yan et al. Stem Cells Dev 2010;19:469-80.*
Atari et al. Journal of Cell Science 2012;125, 3343-3356.*
Kim, D., et al., "Generation of Human Inducted Pluripotent Stem Cells by Direct Delivery of Reprogramming Proteins", Jun. 5, 2009, pp. 472-476, vol. 4, No. 6.
Lizier, N., et al., "Generation of Induced Pluripotent Stem Cells from Dental Pulp Somatic Cells", "Pluripotent Stem Cells", Aug. 23, 2013, pp. 131-149, Publisher: InTech, DOI: 10.5772/55856.
Suh, J., et al., "A Cell-Permeable Fusion Protein for the Mineralization of Human Dental Pulp Stem Cells", "Journal of Dental Research", Jan. 1, 2012, pp. 90-96, vol. 91, No. 1.
Zhang, H., et al,, "Reprogramming of Somatic Cells via Tat-Medicated Protein Transduction of Recombinant Factors", "Biomaterials", Mar. 17, 2012, pp. 5047-5055, vol. 33, No. 20.
Green, M., et al,, "Autonomous Functional Domains of Chemically Synthesized Human Immunodeficiency Virus Tat Trans-Activator Protein", "Cell", Dec. 23, 1988, pp. 1179-1188, vol. 55.
Laus, R., et al, "Enhanced major histocompatibility complex class I-dependent presentation of antigens modified cationic and fusogenic peptides", "Nature Biotechnology", Dec. 2000, pp. 1269-1272, vol. 18.
Ma, H., et al., "Molecular Determinants for Cellular Uptake of Tat Protein of Human immunodeficiency Virus Type 1 in Brain Cells", "Journal of Virology", Mar. 1997, pp. 2495-2499, vol. 71, No. 3.
Schwarze, S., et al., "In vivo protein transduction: intracellular delivery of biologically active proteins, compounds and DNA", "Trends in Pharmacological Sciences", Feb. 2000, pp. 45-48. Volume 21.

(Continued)

*Primary Examiner* — Janice Li
(74) *Attorney, Agent, or Firm* — Hultquist, PLLC; Steven J. Hultquist (57) ABSTRACT

A method of preparing a reprogramming induced pluripotent stem cell from a human-derived somatic cell using a fusion protein in which a reprogramming inducing factor and cell permeable peptide (CPP) are fused, and a fusion protein in which a reprogramming inducing factor and a cell permeable peptide are fused are disclosed.

According to the present invention, the induced pluripotent stem cell having high efficiency and high stability can be prepared by maximizing the effect of the reprogramming inducing transcription factor beyond the existing viral peptide transporter, in inducing the reprogramming of the somatic cell.

3 Claims, 8 Drawing Sheets

(56) References Cited

OTHER PUBLICATIONS

Takahashi, K., et al., "Induction of Pluripotent Stem Cells from Mouse Embryonic and Adult Fibroblast Cultures by Defined Factors", "Cell", Aug. 25, 2006, pp. 663-676, vol. 126.
Takahashi, K., et al, "Induction of Pluripotent Stern Cells from Adult Human Fibroblasts by Defined Factors", "Cell", Nov. 30, 2007, pp. 861-872, vol. 131.
Verma, I., et al., "Gene therapy—promises, problems and prospects", "Nature", Sep. 18, 1997, pp. 239-242, vol. 389.
Vives, E., et al., "A Truncated HIV-1 Tat Protein Basic Domain Rapidly Transiocates through the Plasma Membrane and Accumulates in the Cell Nucleus", "The Journal of Biological Chemistry", Jun. 20, 1997, pp. 16010-16017, vol. 272, No. 25.
Yu, J., et al., "Induced Pluripotent Stem Cell Lines Derived from Human Somatic Cells", "Science", Dec. 21, 2007, pp. 1917-1920, vol. 318.

\* cited by examiner

NI: No induction
I: Induction

CELL PERMEABLE FUSION PROTEIN FOR FACILITATING REPROGRAMMING INDUCTION AND USE THEREOF

CROSS-REFERENCE TO RELATED APPLICATION

This application claims priority under the provisions of 35 U.S.C. §119 of Korean Patent Application No. 10-2013-0102195 filed Aug. 28, 2013. The disclosure of such Korean priority patent application is hereby incorporated herein by reference in its entirety, for all purposes.

TECHNICAL FIELD

The present invention relates to a method of preparing a reprogramming induced pluripotent stem cell from a human-derived somatic cell using a fusion protein in which a reprogramming inducing factor and cell permeable peptide (CPP) are fused, and a fusion protein in which a reprogramming inducing factor and a cell permeable peptide are fused.

BACKGROUND ART

Stem cells have different differentiation potency depending on origins of each stem cell, unlike general somatic cells. Among them, an embryonic stem cell is formed from a blastocyst which is one of the earliest stage of embryonic development, and the most important characteristic of the embryonic stem cell is pluripotent. That is, the embryonic stem cell may be differentiated into most types of cells present in the body including three germ layers of endoderm, mesoderm and ectoderm and regenerated.

However, the main weakness in the embryonic stem cell is that a technology of differentiation into a desired cell is not sufficient, and there is a possibility of forming cancer at the time of transplantation. Due to the problem above, there is a limitation in the development of a cellular therapeutic agent. Nevertheless, research into a technology of developing a therapeutic agent utilizing embryonic stem cells in response to shortage of transplant organs or treatment of genetic diseases and nonrenewable diseases has been continuously conducted.

Yamanaka group established a reprogramming pluripotent stem cell having similar properties to an embryonic stem cell from a fibroblast of a tail of a mouse by over-expressing four reprogramming transcription factors (Yamanaka, S, *Cell*, 126:663-76, 2006). Next year, the Yamanaka group and James A. Thomson group reported that a reprogramming pluripotent stem cell similar to the embryonic stem cell may be formed from a human somatic cell. The two groups used different transcription factors for inducing reprogramming, wherein the Yamanaka group used Oct-4/Sox-2/c-Myc/Klf-4 and Thomson group used Oct-4/Nanog/Sox-2/Lin28 (*Cell.* 131:861-72, 2007; *Science.*, 318(5858):1917-20, 2007). In the early stage, viruses were utilized for over-expression in the reprogramming transcription factor. However, when developing a therapeutic agent using the virus, a stability problem occurred. After that, together with efforts for reducing the number of reprogramming factors, researches for development of a gene combination capable of increasing reprogramming efficiency and methods of inducing reprogramming without using viruses have been conducted.

However, a gene has various problems in that it is not easy to transfer the gene into a cell, in particular, it is significantly difficult to be permeated into a nucleus, a duration in which protein is expressed in a cell is short, and it is significantly difficult to artificially adjust the amount of protein to be expressed in a target cell (Verma, I. M. and Somia, N., *Nature* 389:239-242, 1997). In addition, as an example of methods of transferring the gene, there is an introgression method into a cell by an electrode disturbance by applying an electrical stimulation to a cell membrane. However, the introgression method has a disadvantage in that the number of cells which are stuck to each other due to the damage of the cell membrane and do not grow again corresponds to about 70%. The most commonly used method is a method in which a molecule having a gene surrounded with a lipid membrane as a liposome form is introduced into a cell by endocytosis. In this method, cytotoxicity is not largely caused as compared to an electrical stimulation method. However, when considering that permeation efficiency is significantly deteriorated, it is considered that this experimental method is not the best method, either. On the contrary to the cell permeable method, there is a method of transferring a gene by a virus. Treatment into a cell line which is a host, with Lenti-, Sendai-, Retro viruses as a carrier, allows easy transfer into a cell like a mechanism causing an infection into a human, but also allows genes of the viruses to be inserted into a chromosome. This method is also generally used when inducing over-expressing materials having a large molecular weight such as a therapeutic agent or a gene in a biological experiment in a cell. However, since this method is an experimental method based on viruses, an introgression efficiency is significantly excellent; meanwhile, at the time of being applied to a clinical testing, there is a limitation in that safety may not be secured. Therefore, a method of safer and effectively delivering materials having biological activity into a cytoplasm or a nucleus of a living cell has been demanded.

As a result of research for the demand, a cell permeable peptide (CPP) was suggested. Among researches, a transactivator of transcription (TAT) protein which is a kind of a human immunodeficiency virus type-1 protein has been substantially studied and it is known that TAT protein effectively passes through a cell membrane and is easily transferred into the cytoplasm. It is known that this function is provided due to property of a protein transduction domain, which is the middle domain of the TAT protein (Green, M. and Loewenstein, P. M., Cell, 55:1179, 1988; Ma, M. and Nath, A., J. Virol., 71:2495, 1997). However, it is believed that the TAT domain functions directly on the lipid double-layer of the cell membrane (Vines, E. et al., *J. Biol. Chem.* 272:16010, 1997). However, the CPP is a protein derived from the virus, which is concerned about toxicity. On the other hand, even in the cases of a peptide having amino acid sequences from $339^{th}$ to $355^{th}$ of an antennapedia (ANTP) protein derived from a vinegar fly (*drosophila* sp.) (Schwarze, S. R. et al., *Trends. Pharmacol. Sci.*, 21:45, 2000) and an artificial peptide in which electrically positive amino acids are listed, cell permeability thereof was confirmed by experiments (Laus, R. et al., *Nature Biotechnol.*, 18:1269, 2000).

However, after it was found that in the case of connecting the existing CPP with other peptides or proteins, transportation to the cell of the fusion protein is effective, various applications using the CPP were attempted (Korean Granted Patent No. 568,457), but there has been no attempt of preparing a reprogramming fusion protein in which the virus-derived TAT peptide is not used as a transporter in the country.

Therefore, the present inventors made an effort to develop a more effective method of preparing a reprogramming induced pluripotent stem cell, and found that in the case of directly delivering a cell permeable fusion protein to a target somatic cell instead of inducing the reprogramming of the target somatic cell through the delivery of the genes, the reprogramming of the somatic cell could be induced without genetic modification, such that an induced pluripotent stem cell in which stability of the gene is maintained was capable of being prepared, thereby completing the present invention.

DISCLOSURE

Technical Problem

An object of the present invention is to provide a cell permeable fusion protein for effectively preparing a reprogramming induced pluripotent stem cell.

Another object of the present invention is to provide a method for effectively preparing an induced pluripotent stem cell using the cell permeable fusion protein.

Technical Solution

In order to achieve the foregoing objects, the present invention provides a fusion protein for preparing an induced pluripotent stem cell in which a reprogramming inducing factor and a cell permeable peptide are fused.

In addition, the present invention provides a recombinant polynucleotide encoding the fusion protein for preparing an induced pluripotent stem cell.

Further, the present invention provides a recombinant vector containing the recombinant polynucleotide and a recombinant microorganism transformed with the recombinant vector.

In addition, the present invention provides a method for preparing an induced pluripotent stem cell comprising the steps of: (a) culturing an animal-derived somatic cell in a medium containing the fusion protein for preparing an induced pluripotent stem cell, thereby inducing reprogramming of the somatic cell; and (b) recovering an induced pluripotent stem cell in which reprogramming of the somatic cell is induced.

Advantageous Effects

According to the present invention, the induced pluripotent stem cell having high efficiency and high stability can be prepared by maximizing the effect of the reprogramming inducing transcription factor beyond the existing viral peptide transporter, in inducing the reprogramming of the somatic cell.

BEST MODE

In one aspect, the present invention provides a fusion protein for preparing an induced pluripotent stem cell in which a reprogramming inducing factor and a cell permeable peptide are fused, a recombinant polynucleotide encoding the recombinant fusion protein, a recombinant vector containing the recombinant polynucleotide, and a recombinant microorganism transformed with the recombinant vector.

In order to solve the existing stability problem which may be caused by a virus transporter in transferring or expressing the reprogramming inducing gene into a cell, a fusion protein in which a reprogramming inducing factor is fused with the specific fusion protein, that is, a cell permeable peptide sequence was prepared without delivering the gene into the somatic cell. Then, it was confirmed that in the case of adding the fusion protein to a culture medium and culturing a somatic cell, the protein was effectively introduced into the somatic cell, and the reprogramming was induced.

The reprogramming inducing factor in the present invention is one or more proteins selected from the group consisting of c-Myc, Lin28, Sox2, Klf4 and Oct4.

In the present invention, the cell permeable peptide is a peptide having 70 to 80% of an amino acid selected from the group consisting of arginine, lysine and histidine. Preferably, the cell permeable peptide is one or more selected from the group consisting of a low molecular weight protamine (LMWP) (VSRRRRRRGGRRRR: SEQ ID NO: 2), TAT (YGRKKRRQRRR: SEQ ID NO: 3), penetratin (YGRKKRRQRRR: SEQ ID NO: 4), antennapedia (ANTP: SEQ ID NO: 5), heparin binding domain (HBD) (SSRKKNPNCRRH: SEQ ID NO: 6), D-arginine oligopeptide ($R_8$ or more), and L-arginine oligopeptide ($R_8$ or more).

Figure 1:
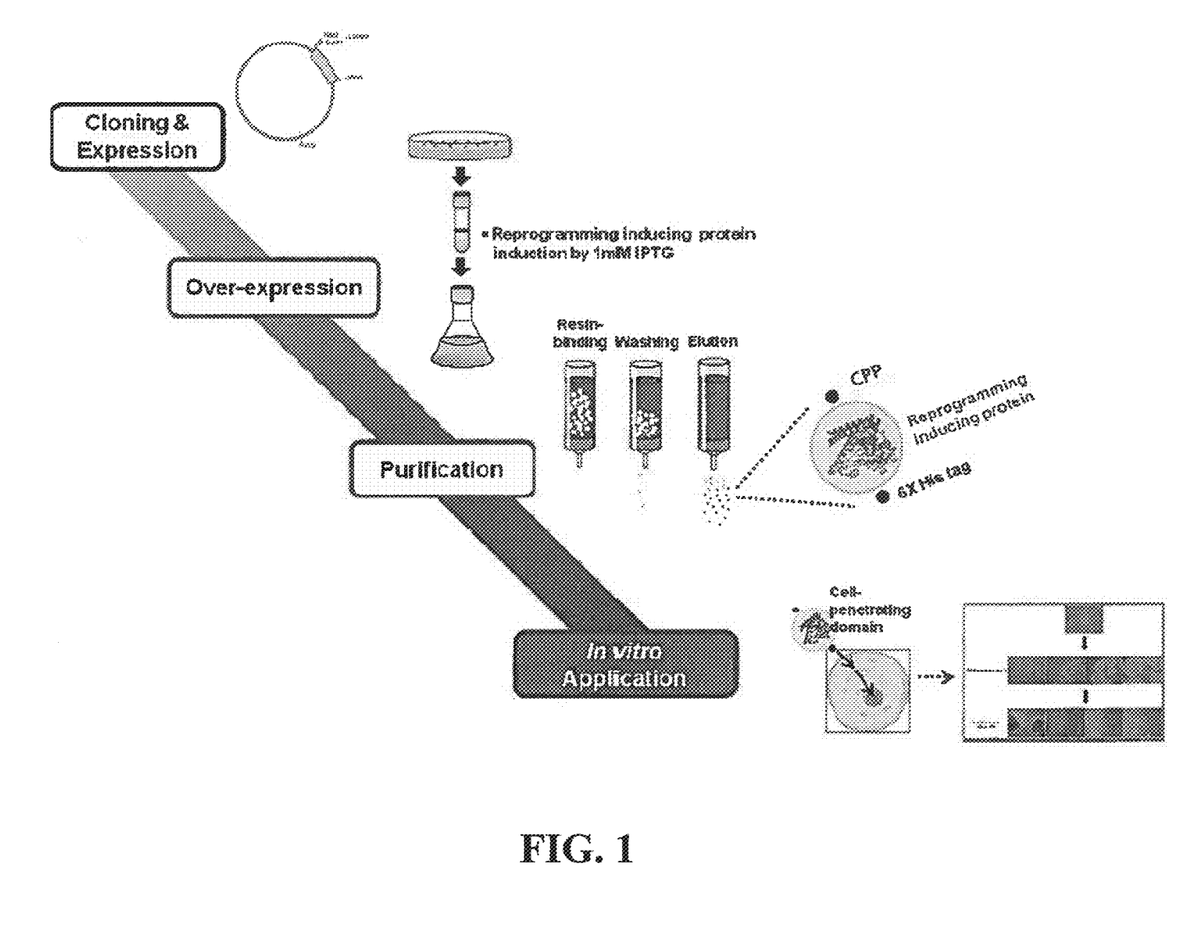
FIG. 1 schematically shows a method for preparing a cell permeable reprogramming fusion protein according to the present invention.
Figure 2A:
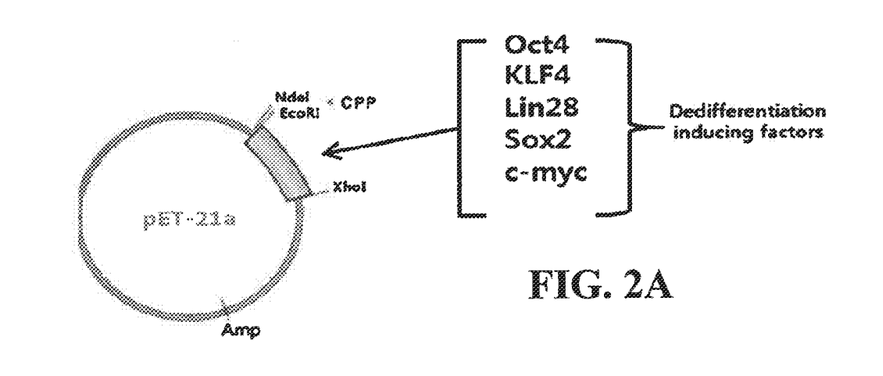
FIG. 2A shows a method for preparing expression vectors (pCPP-c-Myc, pCPP-Lin28, pCPP-Sox2, pCPP-Klf4, pCPP-Oct4) of a cell permeable peptide-reprogramming inducing factor using a pET-21a vector.
Figure 2B:
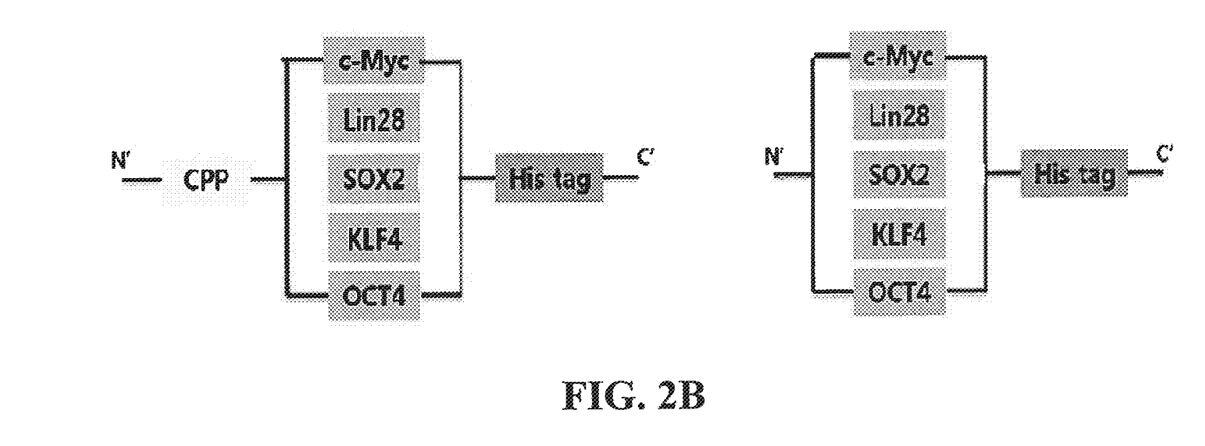
FIG. 2B is a schematic diagram of domains in a fusion protein in which the cell permeable peptide-reprogramming inducing factor is expressed (CPP-c-Myc, CPP-Lin28, CPP-Sox2, CPP-Klf4, CPP-Oct4) and domains in a protein in which a reprogramming inducing factor without cell permeability is expressed as a negative control group (c-Myc, Lin28, Sox2, Klf4, Oct4).

In an embodiment, the present invention provides a CPP-reprogramming inducing factor expression vector capable of over-expressing and easily purifying a CPP-reprogramming inducing factor fusion protein. The expression vectors (pCPP-c-Myc, pCPP-Lin28, pCPP-Sox2, pCPP-Klf4, pCPP-Oct4) included 14 amino acids of human c-Myc, Lin28, Sox2, Klf4, Oct4 and CPP transduction domains (in the present drawings, LMWP was used as CPP, and thus, hereinafter, referred to as an LMWP-reprogramming induced fusion protein). In addition, the present invention provides the recombinant polynucleotide capable of expressing six histidine residues in terminal of the reprogramming inducing factor (see FIGS. 2A and 2B). As the vector, a general TA vector, and the like, can be used, and the expression of the vector may be performed under control of a T7 promoter and a LacO-operator. The LMWP-reprogramming induced fusion protein was over-expressed in E. coli using the expression vector, followed by purification in the denaturalized state by Ni-chelating affinity chromatography. The purification in the denaturalized state means purification after the LMWP-reprogramming induced fusion protein is denaturalized with 4M to 8M urea. Here, in the case of using less than 4M urea, the induction is not easily performed, and in the case of using more than 8M urea, agglomeration is caused.

In another aspect, the present invention provides a method for preparing an induced pluripotent stem cell comprising the steps of: (a) culturing an animal-derived somatic cell in a medium containing the fusion protein for preparing an induced pluripotent stem cell, thereby inducing reprogramming of the somatic cell; and (b) recovering an induced pluripotent stem cell in which reprogramming of the somatic cell is induced.

The present invention is characterized by directly or indirectly co-culturing the somatic cell in which reprogramming is induced in the step (a) and the feeder cell.

In an embodiment of the present invention, a low molecular weight protamine (LMWP) is used as a cell permeable peptide, and five reprogramming inducing proteins (c-Myc, Lin28, Sox2, Klf4 and Oct4) are fused therewith, thereby preparing five kinds of fusion proteins. Transportation of the prepared LMWP-reprogramming induced fusion protein into cytoplasm and a cell nucleus within a short time (60 minutes) in a fibroblast group including a human dental pulp-derived stem cell cultured after a human wisdom tooth was extracted to secure a dental pulp tissue, and the secured dental pulp tissue was pulverized, and then confirmed by a Western blotting method and a confocal fluorescent laser scanning microscope. Meanwhile, a reprogramming inducing protein in which LMWP is not encoded, as a negative control protein, was not transported to the cell.

Most of drug delivery techniques in cells depend on endocytosis using a receptor on a surface of the cell. However, since the peptides show (+) charge, which is completely different from the endocytosis that is one of the existing material transportation mechanisms in the cells, the peptides are dependent on (−) charge of the cell membrane, attached thereto, and delivered, such that materials to be transported to the cells may be effectively and directly introduced within a short time.

The somatic cell derived from human includes human skin, hair, fat, and the like, without limitation.

Figure 7:
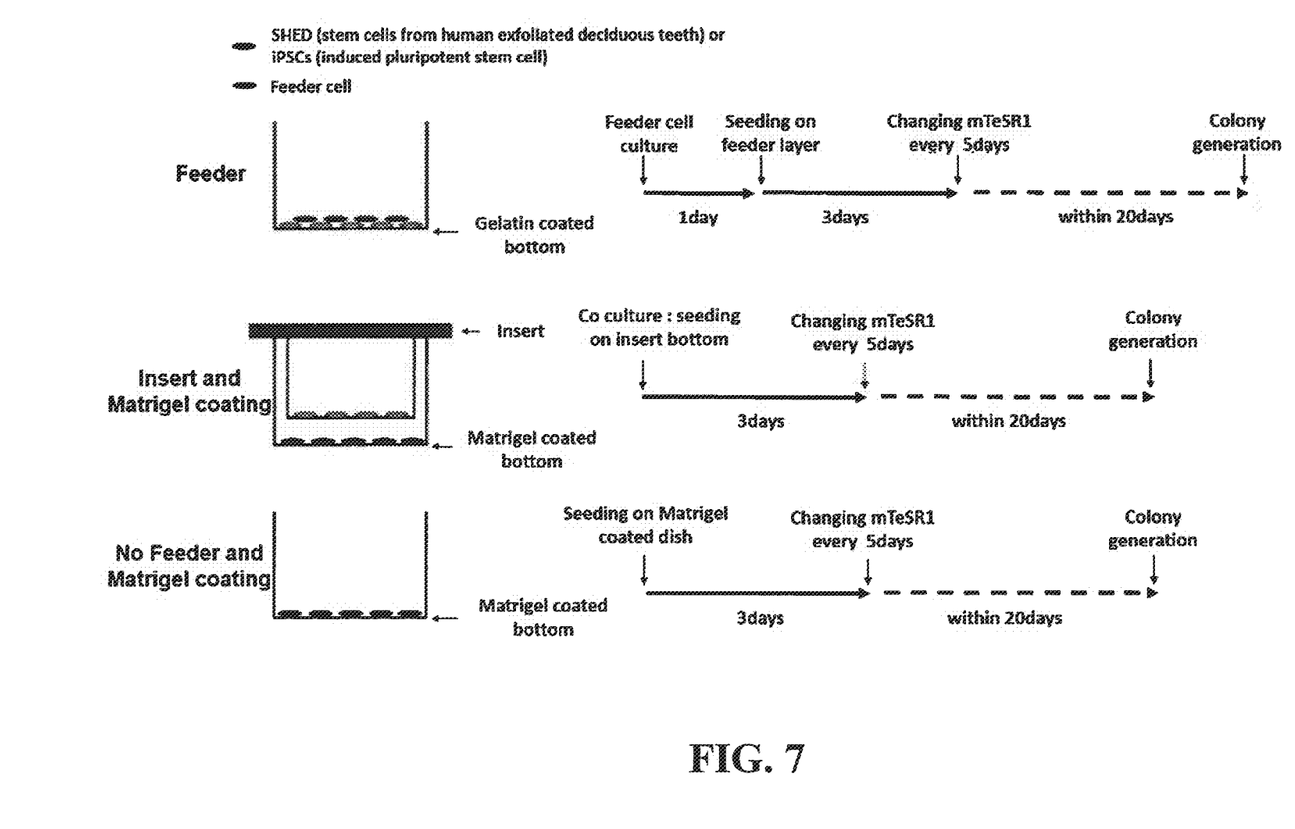
FIG. 7 is a diagram showing three conditions of inducing reprogramming with a primarily cultured human dental pulp-derived cell, including a direct co-culture condition with a feeder cell, an indirect co-culture condition with a feeder cell, and a reprogramming inducing condition without a feeder cell, which shows reprogramming inducing plans according to three conditions.
Figure 8A:
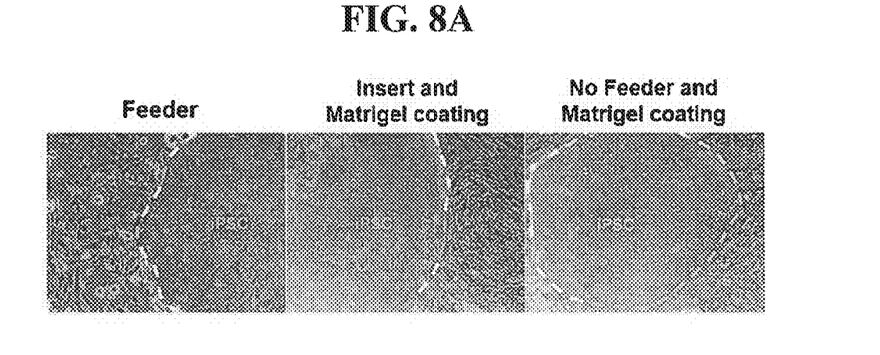
FIG. 8A shows each typical shape of the reprogramming stem cells prepared from three conditions of FIG. 7.
Figure 8B:
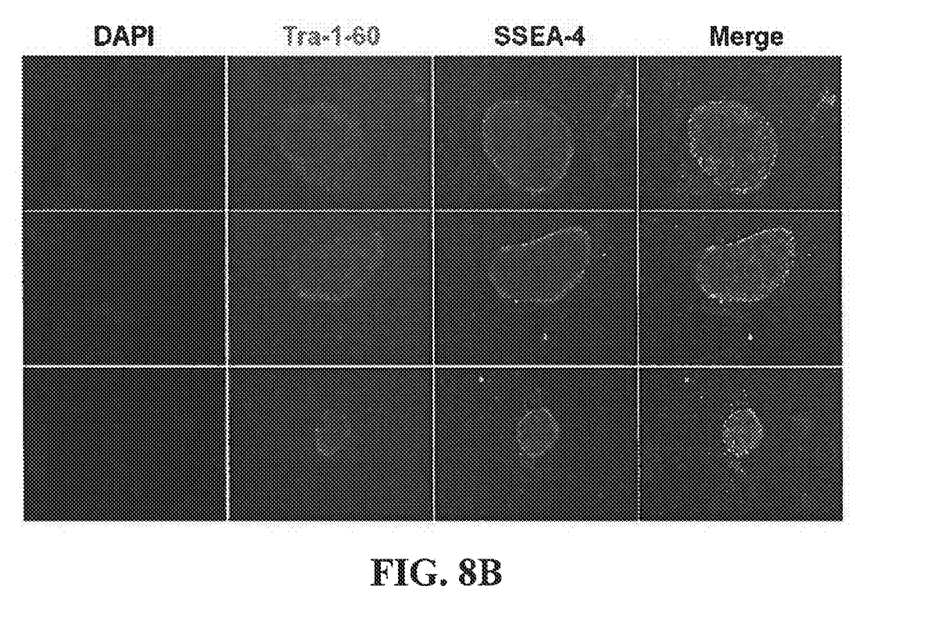
FIG. 8B is a Live-cell imaging fluorescent photograph of Tra-1-60 and SSEA-4 for distinction of partial reprogramming.

Treatment plans of the five fusion proteins include a case of inducing the reprogramming stem cell through direct and indirect co-culture using the feeder cell and a case of inducing the reprogramming stem cell in a culture dish coated with Matrigel without the feeder cell. The case of using the feeder cell and the direct co-culture means that the five fusion protein is treated four times at intervals of five days and then transported to the feeder cell. The case of using the feeder cell and the indirect co-culture means that the cell is cultured in the culture dish coated with Matrigel and then the feeder cell is cultured onto the insert. The five fusion proteins are treated at intervals of five days to induce the reprogramming. In the case of not using the feeder cell, the cell is cultured in the culture dish coated with Matrigel and the five fusion proteins are treated at intervals of five days to induce the reprogramming (FIG. 7). The induced reprogramming stem cell is grown while forming colonies and has a form of a typical embryonic stem cell (FIG. 8A). In addition, as a result of confirming whether or not a complete reprogramming of the reprogramming stem cell is achieved, it was confirmed that Tra-1-60 and SSEA-4 were stained, which means that a complete reprogramming rather than a partial reprogramming was achieved (FIG. 8B).

The medium is a general medium for cell culture containing the fusion protein. As the medium, a medium in which Knock-out Serum Replacement, Non-Essential Amino Acid, basic FGF, penicillin and streptomycin are supplemented in DMEM/F12 may be used or commercially available mTeSR may be used for culture.

The cell permeable reprogramming induced fusion protein according to the present invention may be chemically or biologically fused. However, a biological fusion method is preferred since by-products are less generated. The chemical fusion method is to induce S—S coupling of an amino group of the transcription factor protein and cell permeable peptide using 1,4-bis-maleimidobutane (BMB), 1,11-bis-maleimidotetraethyleneglycol (BM [PEO]4), 1-ethyl-3-[3-dimethyl aminoproyl]carbodiimide hydrochloride (EDC), succinimidyl-4-[N-maleimidomethylcyclohexane-1-carboxy-[6-amido caproate]] (SMCC) and sulfonides thereof (sulfo-SMCC), succinimidyl 6-[3-(2-pyridyldithio)-ropionamido] hexanoate] (SPDP), and sulfonides thereof (sulfo SPDP), m-maleimidobenzoyl-N-hydroxysuccinimide ester (MBS) and sulfonides thereof (sulfo-MBS), succinimidyl[4-(p-maleimidophenyl)butyrate] (SNPB) and sulfonides thereof (sulfo-SMPB), and the like, as a crosslinking agent, wherein the peptide is non-selectively coupled with the amino group of the protein, causing by-products in which a number of peptides are introduced into one protein. However, since the biological fusion method is designed so that one molecular peptide is introduced at the time of constructing a plasmid, a risk of causing by-products is reduced.

All technical and scientific terms used in the detailed description of the present invention have the same meaning as being generally appreciated by those skilled in the art to which the present invention pertains. In general, the nomenclature used in the present specification is well known in technical fields and generally used.

The "cell" used in the present invention means a somatic cell or a stem cell having various origins. The "stem cell" is a blast cell having differentiation potency into various kinds of tissues in the body, and may be largely classified into an embryonic stem cell and an adult stem cell. The "embryonic stem cell", which is a blast cell having differentiation potency, means a cell having pluripotency which is differentiated into various tissue cells under appropriate conditions in an undifferentiated state, and includes embryoid bodies derived from the embryonic stem cell with a wide range. The "adult stem cell" means a cell having a limited differentiation potency which is not capable of being differentiated into every tissue in the body but being differentiated into each target organ. In addition, the "differentiation potency" means a potency in which a portion of the embryo is capable of being differentiated into various kinds of organs or tissues depending on development conditions in the early development of organisms.

The "dedifferentiation" in the present invention means an epigenetic regression process in which a partially or finally differentiated cell is allowed to return to the undifferentiated state such as a pluripotent state or a versatile state, such that new differentiated tissue may be formed. The dedifferentiation phenomenon is possible since it is a reversible process in which epigenetic changes of a cell genome are not fixed but may be erased and may be formed again. The dedifferentiation may be called as "reprogramming" and is directed to a process of changing genetic and expressive profile of the partially or finally differentiated cell so as to be similar to that of the embryonic stem cell. For example, the change includes a change in methylation pattern, a change in an expression rate of a stem cellular gene, and the like.

The "induced pluripotent stem cell" used in the present invention means a stem cell having differentiation potency into all triploblastic cells, including the mesoderm, the endoderm and the ectoderm required for forming biological entities, which indicates ultimate potency of the stem cell. In addition, the pluripotent stem cellular gene means a marker having potency or a gene having potency of inducing the pluripotency, such that the pluripotent stem cellular gene is classified as a reprogramming inducing factor.

The "feeder cell" or the "feeder layer" used in the present invention, which is a cell used for culturing the embryonic stem cell or the reprogramming stem cell, is treated with Mitomycin C or is used in a state in which cell division is stopped by irradiation. As the feeder cell, a mouse embryonic fibroblast (MEF) is usually used and commercially available STO cell line, SNL, or the like, is used. Recently, there is an attempt of excluding foreign materials using a human somatic cell, wherein fibroblasts derived from human tissues may be included.

Hereinafter, the present invention will be described in detail with reference to the following Examples. However, the following examples are only for exemplifying the present invention, and it will be obvious to those skilled in the art that the scope of the present invention is not construed to be limited to these examples.

Example 1

Preparation of Cell Permeable Peptide-Reprogramming Inducing Factor Sequence Conjugate and Transformation In order to over-express five low molecular weight protamine (LMWP: VSRRRRRRGGRRRR)-reprogramming inducing factor fusion proteins and five reprogramming inducing factors without LMWP, the LMWP sequence, the reprogramming inducing factor sequence, and six histidine residues were designed in each pET-21a vector in a continuous sequence, and as a negative control group, the reprogramming inducing factor sequence except for LMWP and six histidine residues were designed in a continuous sequence in each vector, which were entirely shown in FIG. 2A. A total of 10 designed transgenics were requested from Cosmogenetech Co., Ltd. The gene of the reprogramming inducing factor used as the fusion protein was shown in Table 1, and base sequence and amino acid sequence of the cell permeable peptide, that is, LMWP were shown in Table 2. The requested plasmids were transformed into each competent cell (Novagen, BL21 strain, Rosetta 2(DE3)), the transformed *E. coli* BL21 (DE3) were selected, colonies were inoculated into 200 ml medium, and 1 mM of Isopropyl-1-thio-β-D-galactopyranoside (hereinafter, referred to as IPTG; Duchefa, Netherlands) was added to the medium, thereby obtaining a recombinant LMWP-reprogramming factor, followed by over-expression. Each schematic diagram of the expressed protein and the control protein was shown in FIG. 2B.

TABLE 1

| reprogramming inducing factor | Genebank No. |
| --- | --- |
| c-Myc | NM002467 |
| Lin28 | AF521099 |
| Sox2 | NM003106 |
| Klf4 | NM004235 |
| Oct4 | NM002701 |

TABLE 2

| CPP | Type | Sequences |
| --- | --- | --- |
| LMWP | base | GTT TCA AGA AGA AGG AGA AGA AGG GGA GGA AGA AGG AGA AGA (SEQ. 1) |
| | Amino acid | VSRRRRRRGGRRRR (SEQ. 2) |

Figure 3A:
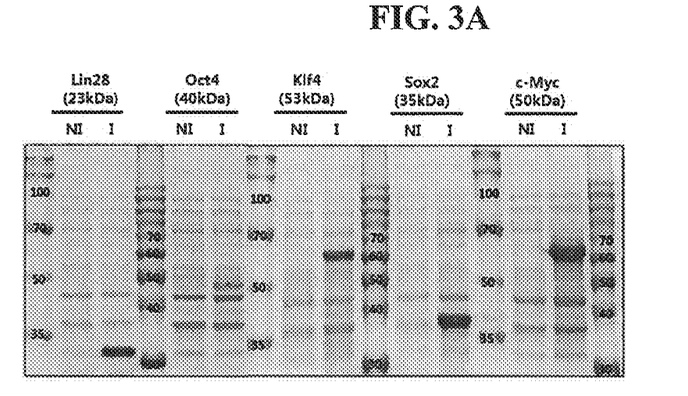
FIG. 3A shows a result obtained by expressing a reprogramming inducing factor protein without cell permeability in E. coli, and performing an electrophoresis on a protein of a group in which the expression is not induced and a protein of a group in which the expression is induced, using a SDS gel.
Figure 3B:
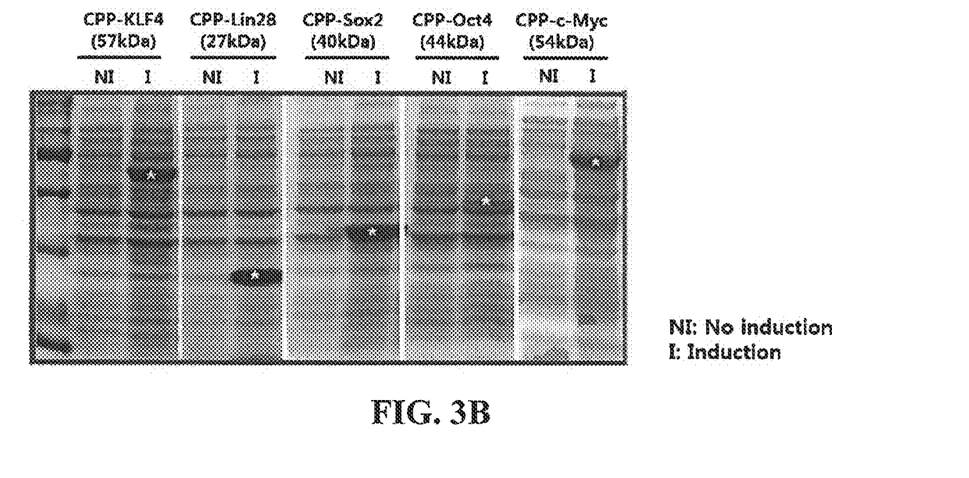
FIG. 3B shows a result obtained by expressing a cell permeable reprogramming fusion protein in E. coli, and performing an electrophoresis on a protein of a group in which the expression is not induced and a protein of a group in which the expression is induced, using a SDS gel.

*E. coli* having the fusion protein over-expressed with IPTG was subjected to cytolysis by BugBuster Master Mix (Novagen, USA), followed by centrifugation, and protein in supernatant was separated by 10% SDS-PAGE electrophoresis. FIG. 3A is a photograph of a control protein stained with Coomassie blue, and FIG. 3B is a stained photograph of the LMWP-reprogramming inducing factor. When comparing a lane in which the over-expression was induced with IPTG to a lane in which the over-expression was not induced, the over-expression portion (shown as white asterisk) was confirmed. Therefore, it was shown that the fusion protein with a high concentration was over-expressed.

Figure 4A:
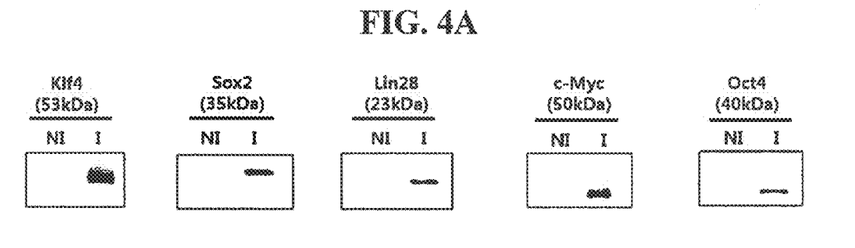
FIG. 4A shows a result obtained by confirming the SDS gel of FIG. 3A by a Western blotting method.
Figure 4B:
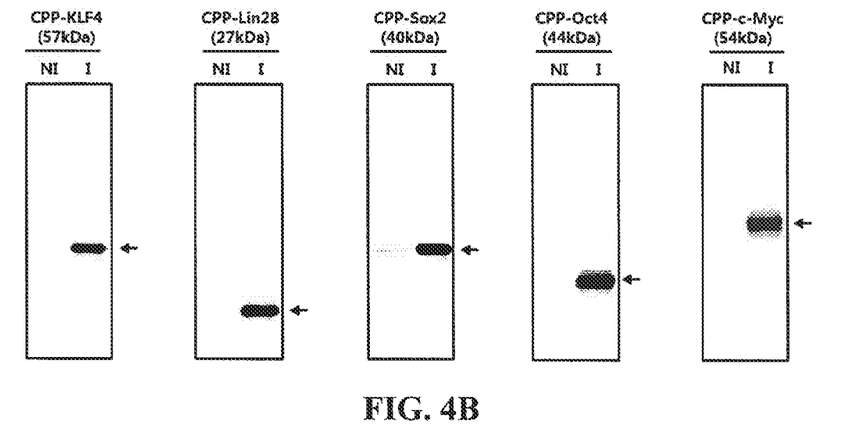
FIG. 4B shows a result obtained by confirming the SDS gel of FIG. 3B by a Western blotting method.

In addition, the fusion protein was determined by a Western blotting method. In order to perform the Western blotting method on the protein separated by SDS-PAGE, the protein was transferred into a nitrocellulose membrane (NC membrane). The NC membrane with the fusion protein transferred thereto was subjected to blocking in 5% skim-milk at room temperature for 1 hour. The NC membrane was washed three times with a TBST solution (prepared by 8.8 g of NaCl, 0.2 g of KCl, 3 g of Tris base, pH 7.4, and 0.05% Tween20 in 1 L solution) for 10 minutes each. The washed NC membrane was reacted with primary antibodies. Since the LMWP-reprogramming inducing factor and the negative control protein have the same protein domain as each other, two proteins could be determined by the same antibody. Two proteins were reacted with 1 μg of c-Myc (Cell Signaling, USA), Lin28 (Cell Signaling, USA), Sox2 (Cell Signaling, USA), Klf4 (Abcam, USA), Oct4 (Santa cluz, USA) antibodies at room temperature for 4 hours. The reacted products were washed three times with TBST for 10 minutes each, followed by reaction with secondary antibodies with horse radish peroxidase (HRP) attached thereto at room temperature for 1 hour. The reacted products were washed three times with TBST for 10 minutes each and photosensitized with an X-ray film in a dark room using an enhanced chemo-luminal (ECL). As a result, it was appreciated from FIG. 4 that the over-expression-induced reprogramming inducing factor protein A and the LMWP-reprogramming inducing factor fusion protein B were observed at the same position as the protein band of FIG. 3.

Example 2

Purification of Recombinant LMWP-Reprogramming Inducing Factor Fusion Protein

Figure 5A:
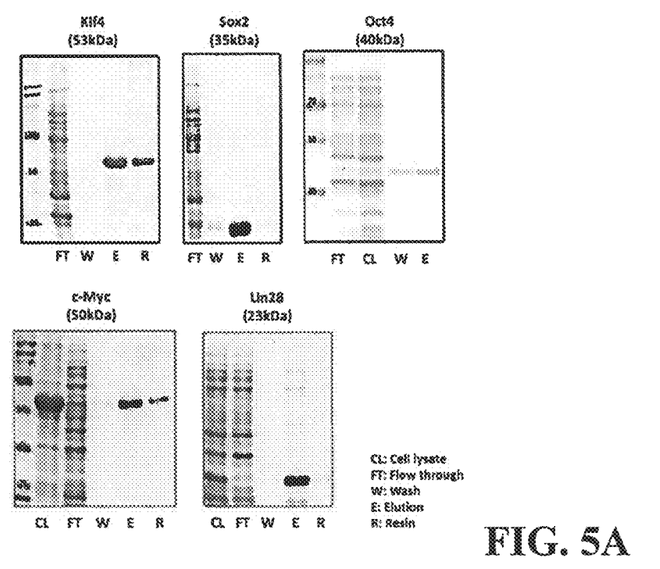
FIG. 5A is a photograph showing an analysis result of a protein fragment collected from each step during a process of expressing a reprogramming inducing factor without cell permeability in E. coli and then performing a purifying process, by 10% SDS-PAGE.
Figure 5B:
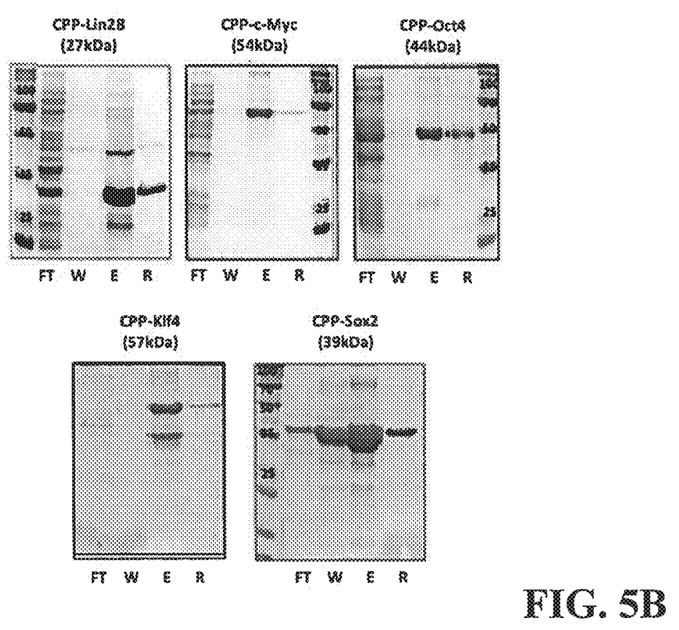
FIG. 5B is a photograph showing an analysis result of a protein fragment collected from each step during a process of expressing a cell permeable reprogramming fusion protein in E. coli and then performing a purifying process, by 10% SDS-PAGE.

In order to increase a purification yield of the fusion protein prepared in Example 1, Example 2 was conducted under denature conditions in which three dimensional structure of the protein was denatured, and 8M urea was put into buffers (Lysis buffer, Washing buffer and Elution buffer) used for purification. The transformed *E. coli* BL21 was put into an LB medium containing ampicillin, and cultured with stirring at a rate of 180 rpm and a temperature of 37° C. When the bacterial concentration in the culture medium, $OD_{600}$ value, was 0.3, IPTG was put into the medium so as to have a concentration of 1 mM. Then, after culturing for 4 hours, over-expression of the protein was induced. After the cultured cells were centrifuged and collected, 10 ml of lysis buffer (50 mM $NaH_2PO_4$, 300 mM NaCl, 10 mM imidazole, 8M urea, pH 8.0) and lysozyme from chicken egg white (Sigma-Aldrich, USA) 10 mg, complete EDTA-free Protease Inhibitor Cocktail (Roche, UK) were put thereinto, followed by reaction for 20 minutes, and sonication. Then, the reacted product was centrifuged at 4° to obtain a supernatant, followed by purification with affinity chromatography using His tag present in the fusion protein. Here, 3 ml slurry of Ni-NTA Agarose resin (Qiagen, USA) was used, and washed with lysis buffer before being put into the column so as to induce equilibrium. Next, the solution containing the fusion protein was injected into the column and allowed to flow, and each 10 ml of wash buffer (50 mM $NaH_2PO_4$, 300 mM NaCl, 20 mM imidazole, and 8M urea, pH 8.0) was allowed to flow twice by gravity. Then, 5 ml of elution buffer (50 mM $NaH_2PO_4$, 300 mM NaCl, 500 mM imidazole, and 8M urea, pH 8.0) was put thereinto and the fusion protein was eluted. In order to confirm the above described state, the product was confirmed by SDS-PAGE, and results thereof were shown in FIG. 5 [A is the control fusion protein, and B is the LMWP-fusion protein)]. Then, fractions containing the fusion protein were collected, followed by PD-10 desalting column (GE Healthcare, Denmark) chromatography to remove salts contained in the fractions, and refolding of the fusion protein at the same time. Since the fusion protein has 6 histidine residues at C-terminal, the fusion protein was purified to be almost pure (purity>90%) by a single stage of an immobilized metal-chelate affinity chromatography. Finally, the fusion protein was lyophilized and protein was obtained.

Example 3

Measurement of In Vitro Cell Permeability of LMWP-Reprogramming Inducing Factor Fusion Protein 3-1: Measurement of Cell Permeability of LMWP-Reprogramming Inducing Factor Fusion Protein by Western Blotting Method In order to confirm the cell permeability of the LMWP-reprogramming inducing factor fusion protein combined with DNA in cellular nucleus and functioned as a transcription factor, the cytoplasm and the nucleus of the fusion protein were separated from each other and confirmed by the Western blotting method. Each $1 \times 10^6$ of fibroblast groups containing the human dental pulp-derived stem cell were divided into 10 cm dish, and incubated overnight in a general medium for stabilizing the cell, for 20 hours. After the incubating overnight for 20 hours, the LMWP-reprogramming inducing factor and the control fusion protein in a concentration of 4 μg/ml were treated for 1 hour and 30 minutes.

Figure 6A:
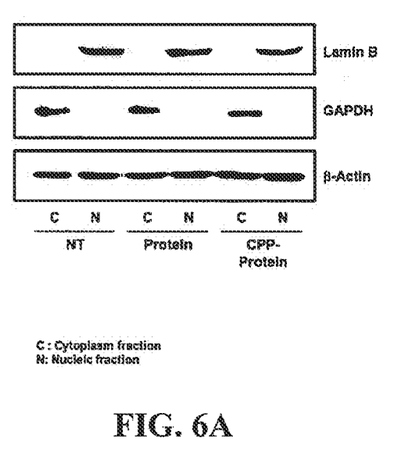
FIG. 6A shows a result obtained by treating the protein (the negative control protein or the cell permeable reprogramming fusion protein) in a human dental pulp-derived cell and then separating a cytoplasm fraction and a nucleic fraction, followed by confirmation with a marker corresponding to the fractions.
Figure 6B:
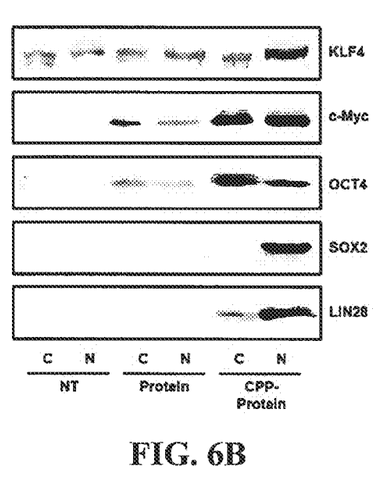
FIG. 6B shows a result obtained by treating the protein (the negative control protein or the cell permeable reprogramming fusion protein) in a human dental pulp-derived cell, and then separating a cytoplasm fraction and a nucleic fraction, followed by confirmation of the permeation degree of the reprogramming factor protein by a Western blotting method.

Then, in order to compare states in which protein in cell was permeated, the cells treated with the LMWP-reprogramming inducing factor and the control fusion protein were separated into the cytoplasm and the nucleus with NE-PER™ Nuclear and cytoplasmic extraction reagents (Pierce, USA) according to the experiment method of the manufacturer. The lysate separated into the cytoplasm and the nucleus was protein-quantified with Bradford's assay, subjected to electrophoresis in 10% polyacrylamide gel with 120 volts for 4 hours, and transferred to a nitrocellulose membrane with a transfer buffer (12.5 mM Tris, 0.1M glycine, pH 8.3) at 310 milliampere (mA) for 2 hours. The membrane was blocked with a blocking solution (5% Nonfat dry milk, in TBS), and a primary antibody solution (c-Myc, Lin28, Sox2; Cell Signaling, USA, Klf4; Abcam, USA, Oct4; Santa Cruz, USA, LaminB, Actin, GAPDH (Glyceraldehyde 3-phosphate dehydrogenase); Santa Cruz, USA) added to the blocking solution so as to have a concentration of 1 μg/ml was reacted overnight at 4° C. In the next morning, the secondary antibody to each primary antibody was added to the blocking solution at a ratio of 1:2000 and reacted at room temperature for 1 hour. The reacted products were photosensitized with an X-ray film in a dark room using an enhanced chemo-luminal (ECL). In order to confirm the separation purity of the cytoplasm and the nucleus, the purity thereof was confirmed by GAPDH which is a marker of the cytoplasm and Lamin B which is a marker of the nucleus, and results thereof were shown in FIG. 6A. As shown in FIG. 6B, it could be confirmed that when observing the amount of the fusion protein fractionized into the cytoplasm fraction and the nucleic fraction and permeated by an antigen-antibody reaction, the fusion protein was introgressed into the nucleus as well as the cytoplasm at each protein concentration treated within a short time (60 minutes). Meanwhile, the negative control protein could not enter into the cell under the same time and the same concentration as the fusion protein.

3-2: Synthesis of LMWP-Reprogramming Inducing Factor Fusion Protein with Fluorescent Marker In order to confirm the cell permeability of the prepared LMWP-reprogramming inducing factor fusion protein, the fusion protein was marked with the fluorescent marker. 1 mg/ml of the prepared protein was dissolved into phosphate buffer (pH 8.5), and fluorescein isothicyanate (FITC) dissolved into dimethyl sulfoxide (DMSO) was mixed therewith, wherein the amount of the FITC corresponds to twice as the calculated value of the molar ratio obtained from the molecular weight of the protein. Here, in order to prevent agglomeration in the combination reaction, the reaction between each 1/10 of the FITC solution and the protein lysate was allowed to be induced at intervals of 10 minutes, followed by shading at 4° C. to induce the combination reaction. Then, the product was purified by reverse phase liquid chromatography for purification. For analysis, 0.1% TFA/H$_2$O and 0.092% TFA/acetonitrile were allowed to flow in C$_{18}$ column having a diameter of 5 cm, with a change of 0 to 60% at a flow rate of 20 ml/min, for 30 minutes. Here, the wavelength of UV detector was set to be 220 nm, and in the case of protein and peptide marked with the fluorescent materials, the wavelength of fluorescence detector was as follows: Ex: 493.5 nm, Em: 460 nm, and the wavelength of UV detector was set to be 220 nm. The only pure fluorescent marked fusion protein was fractionized and freeze-dried.

Figure 6C:
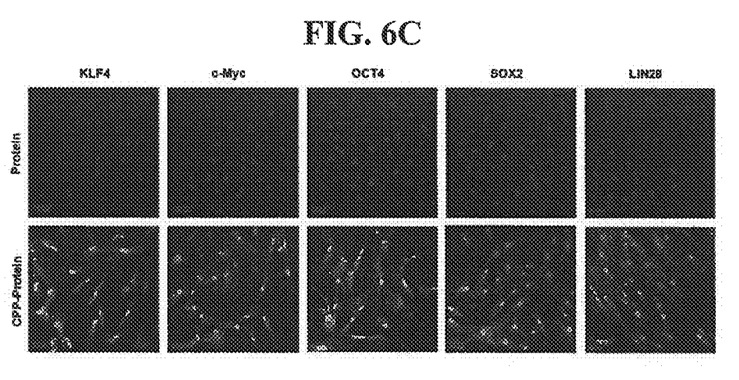
FIG. 6C shows a result obtained by treating the protein (the negative control protein or the cell permeable reprogramming fusion protein) combined with a fluorescent marker in a human dental pulp-derived cell, followed by observation with a confocal fluorescent laser scanning microscope.

3-3: Measurement of Cell Permeability in Fluorescent Image of LMWP-Reprogramming Inducing Factor Fusion Protein In order to measure the degree of cell permeability of the LMWP-Reprogramming Inducing Factor Fusion Protein, 5×10$^4$ cells were divided into 4-well chamber, and in MEM medium not containing fetal bovine serum (FBS), each 4 μg/ml of the fluorescent marked LMWP-reprogramming inducing factor fusion protein prepared by the preparation of Example 3-2 and the negative control protein was injected into each well, then after 1 hour, the product was twice washed with phosphate buffer solution (PBS) and treated with a dye staining the nucleus (Hoechst 33342, blue) at room temperature for minutes. Next, the product was washed twice with phosphate buffer solution (PBS) and was observed by confocal scanning microscope (IX 70, Olympus Co., Tokyo, Japan). As a result, it could be appreciated from FIG. 6C that at the time of treatment with the cell permeable reprogramming inducing factor fusion protein combined with the fluorescent dye prepared by Example 3-2 and the control protein thereof, the introgression into the nucleus as well as the cytoplasm was observed in the fluorescence within a short time (60 minutes). Meanwhile, the negative control protein could not enter into the cell under the same time and the same concentration as the fusion protein.

Example 4

Induction of Reprogramming Stem Cell Using LMWP-Reprogramming Inducing Factor Fusion Protein 4-1: Establishment of Reprogramming Stem Cell Utilizing LMWP-Reprogramming Inducing Factor Fusion Protein Under Direct Co-Culture with a Feeder Cell A mouse embryonic fibroblast treated with mitomycin C was cultured in 6-well plate coated with 0.2% gelatin for 24 hours, in DMEM medium containing 10% FBS. The next day, the primarily cultured human dental pulp-derived mesenchyma stem cell in a concentration of 5×10$^4$ for each well was put thereinto and cultured for three more days. Then, the culture medium was changed every day with 20% Knockout Serum Replacement, 1% Non-Essential Amino Acid, 100 ng/mL basic FGF or mTeSR™1, in the embryonic stem cell culture medium DMEM/F12. The reprogramming inducing medium contained five LMWP-reprogramming inducing factor fusion proteins in each concentration of 8 μg/ml with 20% Knock-out Serum Replacement, 1% Non-Essential Amino Acid, 100 ng/mL basic FGF or mTeSR™1 in DMEM/F12, and the reprogramming inducing medium was put thereinto at intervals of five days. Colonies were shown in 20 days and then the embryonic stem cell culture medium was used (FIG. 7). In order to differentiate the complete reprogramming and the partial reprogramming, live-cell imaging was conducted with Tra-1-60 and SSEA-4. When the colonies in which the complete reprogramming was conducted grew to have a size available for subculture, subculture was performed. It could be confirmed from FIG. 8A that each colony had a typical shape of the embryonic stem cell, and it could be confirmed from FIG. 8B that as staining results with Tra-1-60 and SSEA-4, the complete reprogramming was performed.

4-2: Establishment of Reprogramming Stem Cell Utilizing LMWP-Reprogramming Inducing Factor Fusion Protein Under Indirect Co-Culture with Feeder Cell A mouse embryonic fibroblast treated with mitomycin C was cultured on the insert in DMEM medium containing 10% FBS for 3 days. At the same time, the human dental deciduous pulp-derived mesenchyma stem cell was cultured in a concentration of 5×10$^4$ for each well in the culture dish coated with Matrigel, and after 3 days, the culture medium was changed into the reprogramming inducing medium. The reprogramming inducing medium contained five LMWP-reprogramming inducing factor fusion proteins in each concentration of 8 μg/ml with 20% Knock-out Serum Replacement, 1% Non-Essential Amino Acid, 100 ng/mL basic FGF or mTeSR™1 in DMEM/F12, and the reprogramming inducing medium was put thereinto at intervals of five days. Then, on days in which the reprogramming inducing medium was not put thereinto, the culture medium was changed every day with 20% Knock-out Serum Replacement, 1% Non-Essential Amino Acid, 100 ng/mL basic FGF or mTeSR™1, in the embryonic stem cell culture medium DMEM/F12. Colonies were shown in 20 days and then the embryonic stem cell culture medium was used. When the colonies grew to have a size available for subculture, subculture was performed. Then, in order to differentiate the complete reprogramming and the partial reprogramming, live-cell imaging was conducted with Tra-1-60 and SSEA-4 (FIG. 7). When the colonies in which the complete reprogramming was conducted grew to have a size available for subculture, subculture was performed. It could be confirmed from FIG. 8A that each colony had a typical shape of the embryonic stem cell, and it could be confirmed from FIG. 8B that as staining results with Tra-1-60 and SSEA-4, the complete reprogramming was performed.

4-3: Establishment of Reprogramming Stem Cell Utilizing LMWP-Reprogramming Inducing Factor Fusion Protein without Feeder Cell The primarily cultured human dental pulp-derived mesenchyma stem cell was put into a culture dish coated with Matrigel with a concentration of 5×10$^4$ for each well and cultured for three days. After 3 days, the culture medium was changed into the reprogramming inducing medium. The reprogramming inducing medium contained five LMWP-reprogramming inducing factor fusion proteins in each concentration of 8 μg/ml with 20% Knock-out Serum Replacement, 1% Non-Essential Amino Acid, 100 ng/mL basic FGF or mTeSR™1 in DMEM/F12, and the reprogramming inducing medium was put thereinto at intervals of five days. Then, on days in which the reprogramming inducing medium was not put thereinto, the culture medium was changed every day with 20% Knock-out Serum Replacement, 1% Non-Essential Amino Acid, 100 ng/mL basic FGF or mTeSR™1, in the embryonic stem cell culture medium DMEM/F12. Colonies were shown in 20 days and then the embryonic stem cell culture medium was used. When the colonies grew to have a size available for subculture, subculture was performed. Then, in order to differentiate the complete reprogramming and the partial reprogramming, live-cell imaging was conducted with Tra-1-60 and SSEA-4 (FIG. 7). When the colonies in which the complete reprogramming was conducted grew to have a size available for subculture, subculture was performed. It could be confirmed from FIG. 8A that each colony had a typical shape of the embryonic stem cell, and it could be confirmed from FIG. 8B that as staining results with Tra-1-60 and SSEA-4, the complete reprogramming was performed.

Although specific embodiments of the present invention are described in detail, it will be apparent to those skilled in the art that the specific description is merely a desirable exemplary embodiment and should not be construed as limiting the scope of the present invention. Therefore, the substantial scope of the present invention is defined by the accompanying claims and equivalent thereof.

The invention claimed is:

1. A method for preparing an induced pluripotent stem cell comprising the steps of:
   (a) culturing a dental pulp-derived stem cell in a medium containing a fusion protein in which a reprogramming inducing factor and a cell permeable peptide are fused, wherein said reprogramming inducing factor is one or more protein selected from the group consisting of c-Myc. Lin28, Sox2. Klf4 and Oct4, and wherein said cell permeable peptide is low molecular weight protamine (LMWP, VSRRRRRRGGRRRR), thereby inducing reprogramming of the dental pulp-derived stem cell; and
   (b) recovering an induced pluripotent stem cell in which reprogramming of the dental pulp-derived stem cell is induced.

2. The method of claim 1, wherein the dental pulp-derived stem cell in which reprogramming is induced in the step (a) and a feeder cell are directly co-cultured.

3. The method of claim 1, wherein the dental pulp-derived stem cell in which reprogramming is induced in the step (a) and a feeder cell are indirectly co-cultured.

* * * * *

UNITED STATES PATENT AND TRADEMARK OFFICE
CERTIFICATE OF CORRECTION

PATENT NO. : 9,644,185 B2 Page 1 of 1
APPLICATION NO. : 14/470013
DATED : May 9, 2017
INVENTOR(S) : Yoon Jeong Park et al.

It is certified that error appears in the above-identified patent and that said Letters Patent is hereby corrected as shown below:

In the Specification

Column 11, Line 46: "room temperature for minutes." should be --room temperature for 10 minutes.--.

In the Claims

Column 15, Line 31: "c-Myc. Lin28, Sox2. Klf4 and Oct4," should be --c-Myc, Lin28, Sox2, Klf4 and Oct4,--.

Signed and Sealed this
Twentieth Day of June, 2017

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 6

<210> SEQ ID NO 1
<211> LENGTH: 42
<212> TYPE: DNA
<213> ORGANISM: Artificial
<220> FEATURE:
<223> OTHER INFORMATION: LMWP

<400> SEQUENCE: 1
gtttcaagaa gaaggagaag aaggggagga agaaggagaa ga                     42

<210> SEQ ID NO 2
<211> LENGTH: 14
<212> TYPE: PRT
<213> ORGANISM: Artificial
<220> FEATURE:
<223> OTHER INFORMATION: LMWP

<400> SEQUENCE: 2

Val Ser Arg Arg Arg Arg Arg Arg Gly Gly Arg Arg Arg Arg
1               5                   10

<210> SEQ ID NO 3
<211> LENGTH: 11
<212> TYPE: PRT
<213> ORGANISM: Artificial
<220> FEATURE:
<223> OTHER INFORMATION: TAT

<400> SEQUENCE: 3

Tyr Gly Arg Lys Lys Arg Arg Gln Arg Arg Arg
1               5                   10

<210> SEQ ID NO 4
<211> LENGTH: 11
<212> TYPE: PRT
<213> ORGANISM: Artificial
<220> FEATURE:
<223> OTHER INFORMATION: penetratin

<400> SEQUENCE: 4

Tyr Gly Arg Lys Lys Arg Arg Gln Arg Arg Arg
1               5                   10

<210> SEQ ID NO 5
<211> LENGTH: 4
<212> TYPE: PRT
```

```
<213> ORGANISM: Artificial
<220> FEATURE:
<223> OTHER INFORMATION: antennapedia

<400> SEQUENCE: 5

Ala Asn Thr Pro
1

<210> SEQ ID NO 6
<211> LENGTH: 12
<212> TYPE: PRT
<213> ORGANISM: Artificial
<220> FEATURE:
<223> OTHER INFORMATION: Heparin Binding Domain

<400> SEQUENCE: 6

Ser Ser Arg Lys Lys Asn Pro Asn Cys Arg Arg His
1               5                   10
```